US012748051B2

(12) United States Patent
Shaffer

(10) Patent No.: US 12,748,051 B2
(45) Date of Patent: Sep. 29, 2026

(54) INTEGRATED EXPLOSIVE DETECTOR FOR CONTAINERS AND PACKAGES

(71) Applicant: Greg Shaffer, Verona, NJ (US)

(72) Inventor: Greg Shaffer, Verona, NJ (US)

(73) Assignee: Siruius Solutions, Verona, NJ (US)

( * ) Notice: Subject to any disclaimer, the term of this patent is extended or adjusted under 35 U.S.C. 154(b) by 1074 days.

(21) Appl. No.: 17/893,077

(22) Filed: Aug. 22, 2022

(65) Prior Publication Data

US 2022/0404279 A1 Dec. 22, 2022

Related U.S. Application Data

(63) Continuation-in-part of application No. 16/055,600, filed on Aug. 6, 2018, now abandoned.

(51) Int. Cl.
*G01N 21/64* (2006.01)
*G01N 33/22* (2006.01)

(52) U.S. Cl.
CPC .......... *G01N 21/64* (2013.01); *G01N 33/227* (2013.01)

(58) Field of Classification Search
CPC ............................ G01N 21/64; G01N 33/277
See application file for complete search history.

(56) References Cited

U.S. PATENT DOCUMENTS

2011/0253887 A1 10/2011 Garfinkle et al.
2013/0144131 A1 6/2013 Wang et al.
2013/0217139 A1* 8/2013 Zang .................. G01N 33/0057 422/94
2015/0338319 A1* 11/2015 Ornath .................. G01N 1/405 436/178
2018/0100801 A1* 4/2018 Burn ..................... C07C 211/54

FOREIGN PATENT DOCUMENTS

CN 101163558 A 4/2008
WO 2014134217 A1 9/2014

OTHER PUBLICATIONS

Definition of 'Cloth'. Dictionary.com. Retrieved Apr. 26, 2022, 7 Pages (Year: 2022).

* cited by examiner

*Primary Examiner* — Charles Capozzi
*Assistant Examiner* — Alex Ramirez
(74) *Attorney, Agent, or Firm* — Genius Patent APC; Bruce Angus Hare

(57) ABSTRACT

A cost-effective and limited interaction explosive detector for dangerous, illegal, and/or illicit substances such as explosives, flammable or volatile fluids, and/or other appropriate substances is described. The explosive detector may be integrated into various containers or packages, such as cardboard boxes, paper envelopes, metal shipping containers, and/or other containers or packaging. The integrated explosive detector may provide a visual indication when a subject substance is encountered. The integrated explosive detector may include a port or vent that allows for ambient flow of fluids, such as air, between an interior of the container and the outside environment.

14 Claims, 8 Drawing Sheets

INTEGRATED EXPLOSIVE DETECTOR FOR CONTAINERS AND PACKAGES

CROSS-REFERENCE TO RELATED APPLICATIONS

This application is a continuation-in-part of U.S. patent application Ser. No. 16/055,600, filed on Aug. 6, 2018. U.S. Patent Publication Number 2020/0041474 A1, published on Feb. 6, 2020 is incorporated by reference herein.

BACKGROUND

Various and types of containers or packages, such as those used for air shipments, luggage, shipping containers, boxes, envelopes, mailers, etc. may be used to transport illegal, dangerous, or illicit substances, such as explosives. Such containers and packages may be associated with various types of cargo and/or methods of transport.

Existing solutions require dedicated screening devices that may include expensive components and require items to be examined individually in a serial manner that is time-consuming and costly in itself.

Therefore there exists a need for a low-cost ambient detection solution that is able to be implemented across a variety of containers and does not require external equipment to operate.

BRIEF DESCRIPTION OF THE SEVERAL VIEWS OF THE DRAWING

The novel features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide cost-effective and limited interaction ways to sense dangerous, illegal, and/or illicit substances such as explosives, flammable or volatile fluids, and/or other appropriate substances. An explosive detector of some embodiments may be integrated into various containers or packages, such as cardboard boxes, paper envelopes, metal shipping containers, and/or other containers or packaging able to house goods or other items (e.g., plastic or composite containers).

In some embodiments, the integrated explosive detector may provide a visual indication when a subject substance (i.e., a substance that is detected by the integrated explosive detector) is encountered. For instance, the integrated explosive detector may include a portion that is visible on or at the outside of the container that changes color when a subject substance is encountered.

Subject substances may include substances and/or compounds such as nitroaromatic explosives, nitrate ester and nitramine explosives, inorganic explosives, chlorates, peroxides, and/or other such substances. Examples of such substances include trinitrotoluene (TNT), dinitrotoluene (DNT), royal demolition explosive (RDX), high melting explosive (HMX), pentaerythritol tetranitrate (PETN), composition 4 (C-4), PE-4, Composition B, etc.).

The integrated explosive detector may include a port or vent that allows for ambient flow of fluids, such as air, between an interior of the container and the outside environment. This is in contrast to existing solutions which require a suction device or other pump to induce air flow between the interior and exterior of a container. Further, the ambient flow detection allows multiple containers to be tested at the same time, with the results able to be evaluated as each container is encountered. This is in contrast to existing solutions that utilize a dedicated screening device, animal, and/or technician and test kit to evaluate each container individually and in a serial manner.

The integrated explosive detector may include elements or layers that may be combined in various appropriate ways. For instance, some embodiments may include one or more base or substrate elements, detection elements, and/or protective elements.

In some embodiments, the integrated explosive detector may include multiple zones, where each zone may be associated with a different subject substance, substances, and/or substance type.

Figure 1:
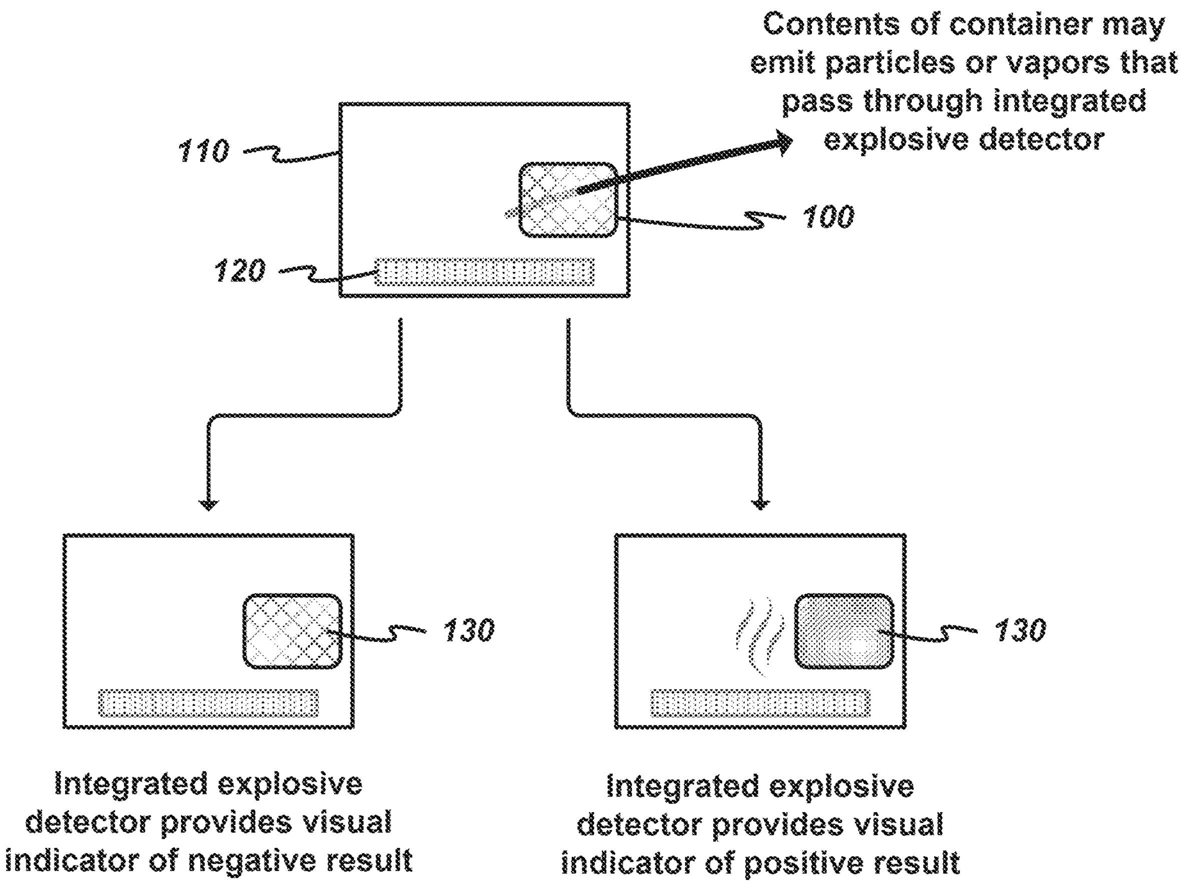
FIG. 1 illustrates an example overview of one or more embodiments described herein, in which an integrated explosive detector of some embodiments is associated with a container and evaluates contents of the container.

FIG. 1 illustrates an example overview of one or more embodiments described herein, in which an integrated explosive detector 100 of some embodiments is associated with a container 110 and evaluates contents 120 of the container 110. The container 110 in this example may be a cardboard box having a cuboid shape. The integrated explosive detector 100 may be associated with various different types of containers 110. The contents 120 may be any items, substances, etc. that may be housed by the container 110.

Container 110, and the term "container" as used herein, may be, utilize, and/or include any receptacle in which material may be held or carried. Examples of container 110 may include, for instance, boxes (e.g., cardboard boxes, plastic boxes, metal boxes, etc.), envelopes (e.g., paper envelopes, plastic envelopes, etc.), shipping containers (e.g., metal cargo containers, freight containers, dry boxes, etc.), crates, and/or other containers or packaging able to house or carry items (e.g., plastic bags, foil pouches, bins made from composite materials, etc.).

The integrated explosive detector 100 may be visible at the exterior of container 110 such that the integrated explosive detector 100 may be evaluated by a technician or device (e.g., a camera and/or other sensor(s)). For instance, the integrated explosive detector 100 may provide a visual indicator 130 that is able to be scanned by a camera associated with a user device such as a smartphone, dedicated cargo scanning equipment, etc.

As shown, in this example the integrated explosive detector 100 may provide a visual indicator 130 of a negative result. In this example, the visual indicator of a negative result is unchanged from an initial appearance of the integrated explosive detector 100, as indicated by the cross-hatch fill patterns. Some embodiments of the integrated explosive detector 100 may provide an indication of a negative result, such as a symbol (e.g., an "O") or change in color.

As shown, in this example the integrated explosive detector 100 may provide a visual indicator 130 of a positive result. In some embodiments, the visual indicator may be a change in color, as indicated by the change in fill pattern.

The visual indicators of a negative result or positive result may be associated with various types of light sources, sensors, etc. For instance, the visual indicators may be visible under visible light, ultraviolet light, infrared, etc. Different visual indicators may be used for different types of scanners or evaluation. Some embodiments of the integrated explosive detector 100 may include multiple types of visual indicators, such as a visible light indicator and an ultraviolet light indicator. In addition to, or in place of, a discrete indicator, as shown, some embodiments of the integrated explosive detector 100 may include relative indicators, such as different indicators associated with different threshold concentrations of detected substances being indicated by color density or change relative to initial color or other change in visual appearance. As another example, photoluminescent elements may indicate relative concentrations by the amount of emitted light. As still another example, some embodiments of the integrated explosive detector 100 may include multiple discrete indicators associated with different concentrations of detected substances (e.g., an "X" symbol indicating a first concentration threshold, an "XX" symbol indicating a second concentration threshold, etc.).

The integrated explosive detector 100 may be utilized with, by, and/or via other devices, systems, and/or components. For instance, the integrated explosive detector 100 may collect sample material emitted by contents 120 such that the collected sample material may be evaluated by a device such as a handheld portable mass spectrometer.

Integrated explosive detector 100 may provide a visual result indicator based on ambient air flow via the integrated explosive detector 100 (e.g., air flow between an inside and outside of container 110). Throughout this disclosure, "ambient" airflow and/or other ambient conditions may refer to conditions that are encountered by the container during a normal course of packing, transport, etc., without requiring container-specific interactions, such as use of dedicated pressure-inducing equipment such as vacuums or blowers, connectors or other apparatus to engage a container, and/or other additional or detection-specific actions. For instance, a container may be subjected to ambient changing atmospheric pressure throughout the course of air transport (e.g., takeoff, landing, travel at altitude, cabin pressurization and/or depressurization, etc.). As another example, containers may be subjected to ambient heating and/or cooling during storage and/or transport (e.g., based on temperature changes at a storage facility, changes in elevation during transport, etc.).

Figure 2:
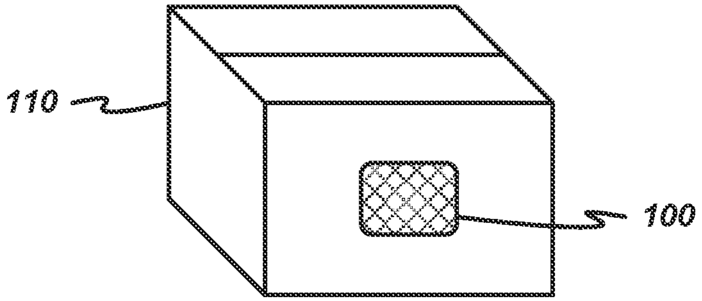
FIG. 2 illustrates a perspective view an integrated explosive detector of one or more embodiments described herein, associated with a box.
Figure 3:
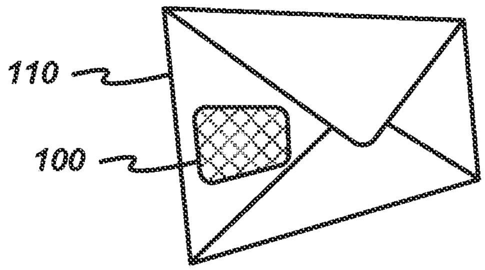
FIG. 3 illustrates a perspective view of an integrated explosive detector of one or more embodiments described herein, associated with an envelope.
Figure 4:
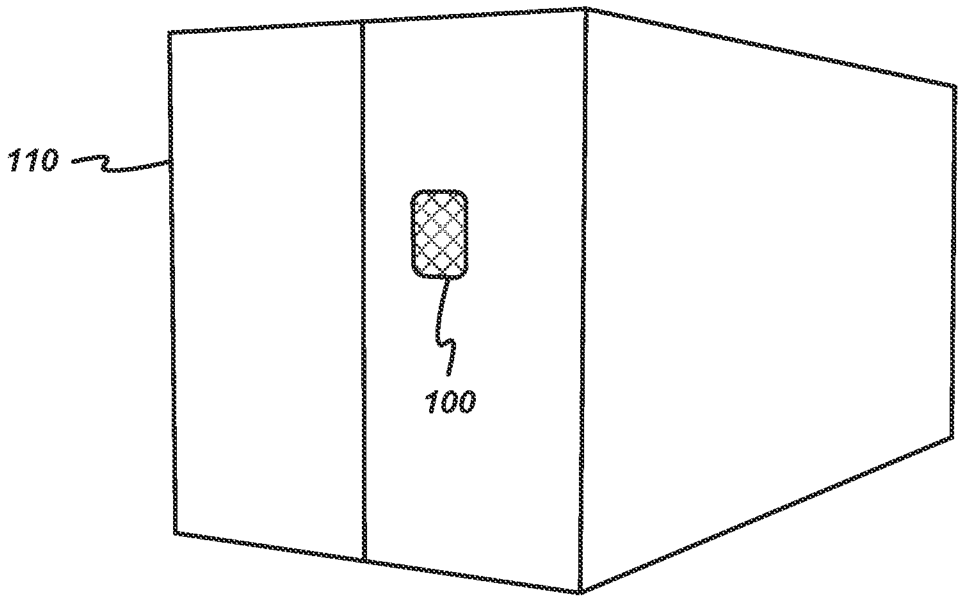
FIG. 4 illustrates a perspective view of an integrated explosive detector of one or more embodiments described herein, associated with a shipping container.

FIG. 2 illustrates a perspective view of an integrated explosive detector 100, associated with a box 110. FIG. 3 illustrates a perspective view of an integrated explosive detector 100, associated with an envelope 110. FIG. 4 illustrates a perspective view of a shipping container 110 with an integrated explosive detector 100, associated with a shipping container 110.

One of ordinary skill in the art will recognize that integrated explosive detector 100 may be associated with various other types of containers or packages 110 and may be integrated in various appropriate ways. Further, although various examples throughout may refer to a specific type of container 110 (e.g., a cardboard box), similar features and/or components may be implemented and/or utilized with other types of containers. In some cases, a container 110 may include multiple integrated explosive detectors 100. For instance, a cuboid shipping container 110 may include an integrated explosive detector 100 associated with each vertical face, a cuboid cardboard box container 110 may include an integrated explosive detector 100 associated with each of the six faces, and an envelope container 110 may include an integrated explosive detector 100 associated with the front and back of the envelope.

The integrated explosive detector 100 may be located such that containers 110 may be easily scanned and/or otherwise evaluated. For instance, an integrated explosive detector 100 may be located at a center of a cuboid face if a cardboard box 110. As another example, an integrated explosive detector 100 may be located on a rear face of an envelope 110, and, more specifically, may be located at the bottom right corner of the rear face of the envelope 110.

Figure 5:
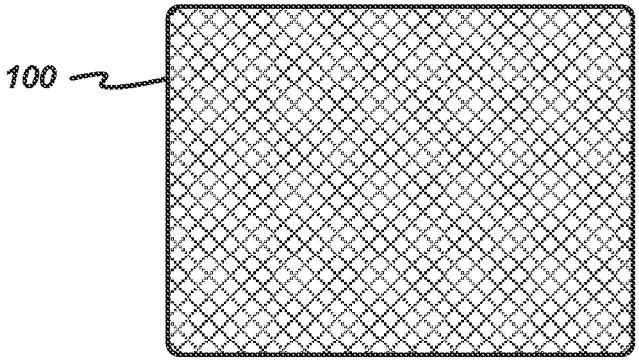
FIG. 5 illustrates a front view of an integrated explosive detector of one or more embodiments described herein.

FIG. 5 illustrates a front view of an integrated explosive detector 100. In this example, the integrated explosive detector 100 has a rectangular shape. Different embodiments may include integrated explosive detectors 100 having various different shapes (e.g., elliptical, square, triangular, polygonal, irregular, etc.). The size of the integrated explosive detector 100 may depend on the size of the associated container 110 and may generally be sized such that the integrated explosive detector 100 is visible from an appropriate distance and/or under other appropriate conditions (e.g., ambient lighting, movement speed, etc.). For instance, business sized envelope containers 110 may be associated with an integrated explosive detector 100 that is similar in size to a postage stamp or other feature of existing shipment channels. As another example, a shipping container 110 may be associated with an integrated explosive detector 100 that is sized to be visible to the human eye from a distance of fifty feet.

In some embodiments, the integrated explosive detector 100 may include indicators other than visual indicators. For instance, a wireless signal may be generated by the integrated explosive detector 100.

Figure 6:
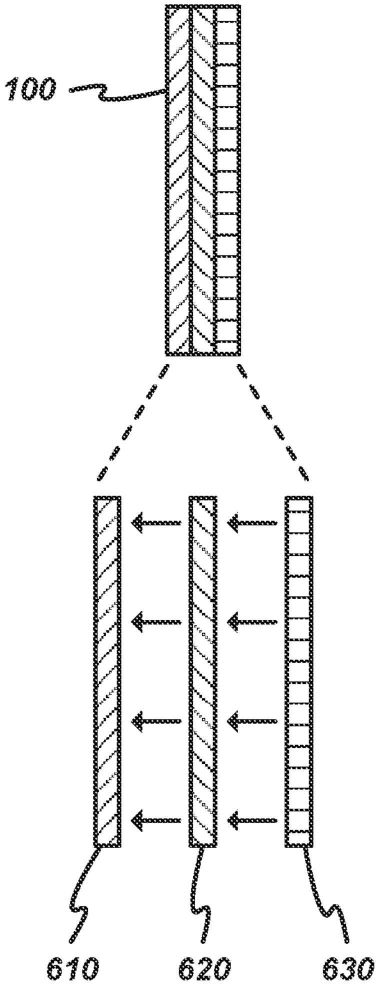
FIG. 6 illustrates a left-side view of an integrated explosive detector of one or more embodiments described herein.

FIG. 6 illustrates a left-side view of an integrated explosive detector 100. As shown, the integrated explosive detector 100 may include a base or substrate element 610, a detection element 620, and a protective element 630. This example includes three elements or layers 610-630, but different embodiments may include a single element up to any number of included elements.

Base or substrate element 610 may support and/or provide structural integrity to, the other elements 620-630, and/or couple the integrated explosive detector 100 to container 110. Base or substrate element 610 may include a frame or other support structure (e.g., a plastic, metal, paper, and/or cardboard frame or skeleton). Substrate element 610 may be, or include, adhesive in some embodiments, such that the substrate element 610 may couple the integrated explosive detector 100 to the container 110, and/or couple to other elements of the integrated explosive detector such as the detection element 620.

Detection element or "semi-permeable filter" 620 may be or include materials that may allow ambient air to flow from the interior to the exterior of container 110. For instance, detection element 620 may include, utilize, or be, materials such as felt (and/or other textile material(s) produced by matting, condensing, and/or pressing fibers together), cloth or fabric (e.g., woven cloth or fabric), screens, nanowire mesh, painted or deposited nanoparticles or nanowires, etc. Such detection elements 620 or features may provide visual indications (e.g., by emitting light, changing color, etc.) evaluation results. In order to provide such visual indications, detection element 620 may include detection components or features such as, for example, photoluminescent polymers (e.g., photoluminescent polymer optical fiber) and/or colorimetric substances that are activated by the presence of substances such as nitroaromatic explosives, nitrate ester and nitramine explosives, inorganic explosives, chlorates, peroxides, and/or other such substances.

Protective element 630 may be or include materials that may provide structural support and/or protection to other elements of the integrated explosive detector 100. For instance, protective element 630 may include a rigid metal or plastic plate that prevents removal of, or damage to, the other components of integrated explosive detector 100. As another example, protective element 630 may include a screen or mesh layer. In some embodiments, protective element 630 may also serve as the base or substrate element 610 and/or otherwise provide similar functionality (e.g., by coupling to the container 110).

In some embodiments, protective element 630 may include visual indicators (e.g., labelling) and/or other visual features. For instance, some portion of protective element 630 may include a lens or optical filter that may affect the appearance of light emitted from detection element 620 (e.g., by changing the brightness or color of the emitted light, by attenuating certain wavelengths of light, etc.).

Depending on the type of container 110, the elements 610-630 may be flexible or rigid to varying degrees. Each element 610-630, or portions thereof, may allow fluid such as air to pass through the element and the integrated explosive detector 100. For instance, a protective element 630 associated with a metal container may also be made of metal or other rigid material and may offer similar rigidity or structural integrity as the container itself. As another example, a protective element 630 associated with a paper envelope 110 may offer similar rigidity as the paper. Further, the elements 610-630 may be sized as appropriate for the container. For instance, a detection element 620 for a paper envelope 110 may have a thickness that is less than the paper stock used for the envelope. As another example, the thickness of the elements 610-630 may be sized such that the integrated explosive detector 100 has a same thickness as a cardboard box container 110.

Different embodiments of the integrated explosive detector 100 may include various different elements and/or arrangements of elements than shown. For instance, some embodiments may include a second protective element 630 that may protect the other face of the detection element 620 and/or base element 610. As another example, the protective element 630 may be coupled to the base element 610, with the detection element 620 held in place between the other elements.

As another example, some embodiments of the integrated explosive detector 100 may include a single element or layer that may integrate or otherwise include multiple elements and/or provide similar functionality to those multiple elements. For instance, a felt-based detection element 620 may include an embedded frame or support that serves as the base element 610 and/or protective element 630. As another example, a felt-based or fabric-based detection element 620 may have sufficient strength (e.g., based on thickness of the felt, weight of yarn or thread used to weave the fabric, materials used, etc.) to serve as the base element 610 and/or protective element 630 without any other structure or support.

As another example, various elements may be fused or formed as a single element. For instance, the detection element 620 may include nanofibers that are fused to a metal or plastic base element 610 and/or protective element 630.

As another example, a single element or layer may be divided into multiple elements or layers. For instance, base element 610 may include multiple layers in some embodiments (e.g., a pair of supports may sandwich or bracket the detection element 620).

As another example, the elements or layers may be arranged in a different order or orientation than shown. For instance, the detection layer 620 may be located at one face of the base layer 610 while the protective layer may be located at the opposite face of the base layer 610.

One of ordinary skill in the art will recognize that integrated explosive detector 100 may be otherwise implemented without departing from the scope of the disclosure. For instance, in this example, the layers 610-630 are shown as being a same size, but different embodiments may include differently sized layer or elements 610-630. For example, protective element 630 may have a larger face than detection element 620 and/or base element 610. Further, one of ordinary skill in the art will recognize that the elements 610-630 may have different thicknesses than each other, and/or otherwise be differently shaped.

Different embodiments may include various different couplings between elements 610-630, as necessary. For instance, adhesives or fasteners may be used to couple each element 610-630 to each associated element 610-630. As another example, the elements 610-630 may be pressed or formed as a single device or component. As another example, the elements 610-630 may be integrated with and/or coupled to various features of container 110. For instance, portions of a cardboard box 110 may provide support for portions of the integrated explosive detector 100, where the integrated explosive detector 100 may be coupled using adhesives and/or may be formed as an integrated or embedded feature of the cardboard box 110.

Figure 7:
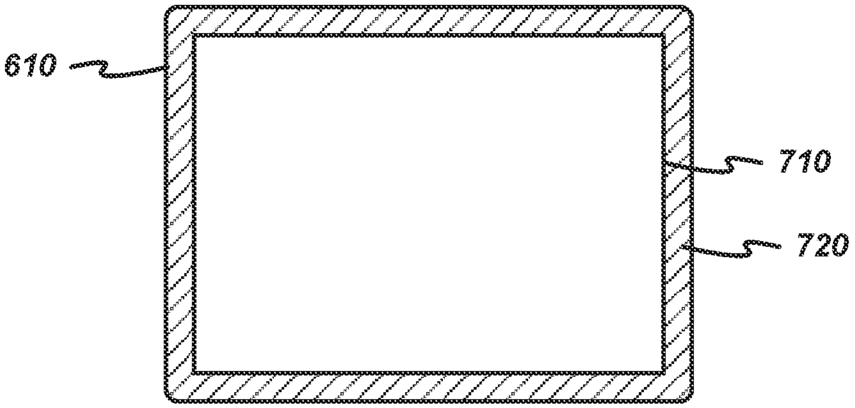
FIG. 7 illustrates a front view of a base or substrate element of an integrated explosive detector of one or more embodiments described herein.

FIG. 7 illustrates a front view of a base or substrate element 610 of an integrated explosive detector 100. In this example, the base element 610 includes a port 710 and a surround 720. Each port 710 may be, or include, one or more openings or holes in a surface of the container 110 that allows ambient airflow between the interior and exterior of the container 110. Throughout this disclosure, the term "surface", in reference to a container 110, may include an exterior wall and/or face of the container 110 and/or any structural or other elements associated therewith (e.g., a wall of a cardboard box associated with a face of the box, a multi-layer portion of a padded envelope associated with an outer surface of the padded envelope, etc.).

Frame or surround 720 may provide structural support to the base element 610 and/or the integrated explosive detector 100 (or a component thereof) if no base element 610 is included. Frame or surround 720 may be securely coupled to the container 110 such that air flow through the port 710 is provided to the detection element 620 (e.g., detection element 620 may at least partially obstruct port 710). A sealed connection between the integrated explosive detector 100 and the container 110 is not required, as long as some portion of ambient air flow between the inside and outside of container 110 may pass through detection element 620. In some embodiments, frame or surround 720 may include, utilize, or be, a portion of the container 110. For instance, if the container 110 is a cardboard box, frame or surround 720 may be a portion of the cardboard box 110 surrounding a hole in one wall or face of the cardboard box 110. As another example, frame or surround 720 may be coupled to a portion of a cardboard box or other container 110 that is located about port 710 via adhesive (e.g., frame or surround 720 may include a plastic frame with peel-and-stick adhesive backing).

Figure 8:
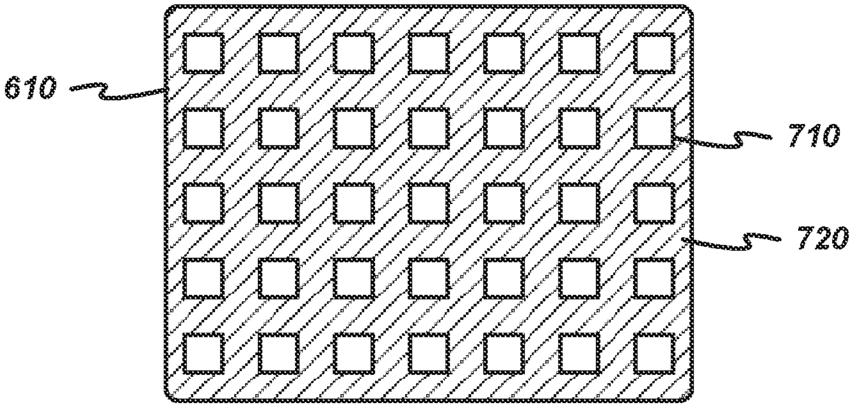
FIG. 8 illustrates a front view of an alternative base or substrate element of an integrated explosive detector of one or more embodiments described herein.

FIG. 8 illustrates a front view of an alternative base or substrate element 610 of an integrated explosive detector 100. In this example, the base element 610 includes a number of ports 710 arranged in a grid or matrix distributed throughout the surround 720.

Figure 9:
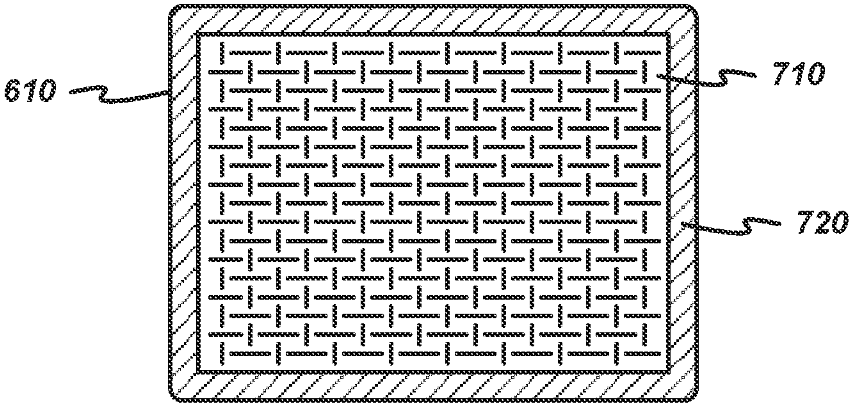
FIG. 9 illustrates a front view of another alternative base or substrate element of an integrated explosive detector of one or more embodiments described herein.

FIG. 9 illustrates a front view of another alternative base or substrate element 610 of an integrated explosive detector 100. In this example, the port 710 includes a mesh fabric that may provide structural support and allow fluid to flow. Surround 720 may be coupled to the fabric port 710 in various appropriate ways (e.g., adhesive, stitching or sewn attachment, etc.).

Different embodiments may include various different bases or substrate elements 610 that may include ports 710 such as round through-holes, slots, gaps in woven fabric, etc. Some embodiments may include multiple base or substrate element 610 types or components. For instance, in some embodiments, the substrate element 610 may include a matrix of slot-type ports 710 that are at least partially covered by a woven fabric port 710.

Figure 10:
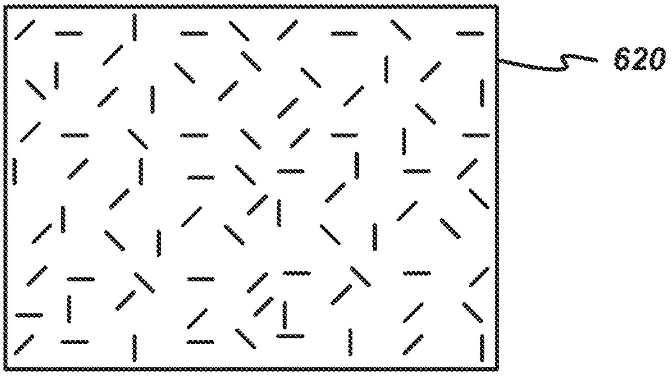
FIG. 10 illustrates a front view of a detection element of an integrated explosive detector of one or more embodiments described herein.

FIG. 10 illustrates a front view of a detection element 620 of an integrated explosive detector 100. In this example, the detection element 620 may include, utilize, or be a material such as felt. The felt material may include various types of fibers that may be adhered together (e.g., via adhesive, compression, and/or other ways).

Figure 11:
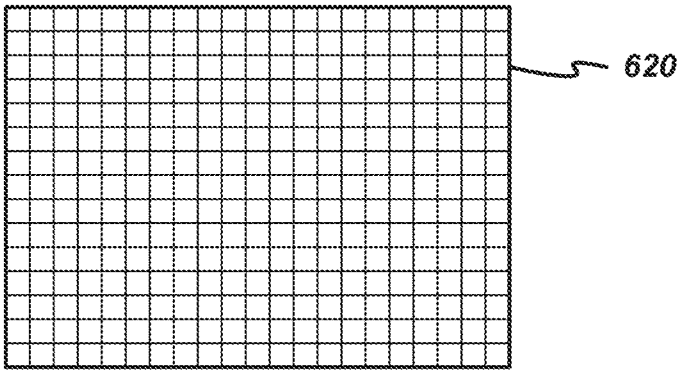
FIG. 11 illustrates a front view of an alternative detection element of an integrated explosive detector of one or more embodiments described herein.

FIG. 11 illustrates a front view of an alternative detection element 620 of an integrated explosive detector 100. In this example, the detection element 620 may include a nanowire grid, as shown.

Figure 12:
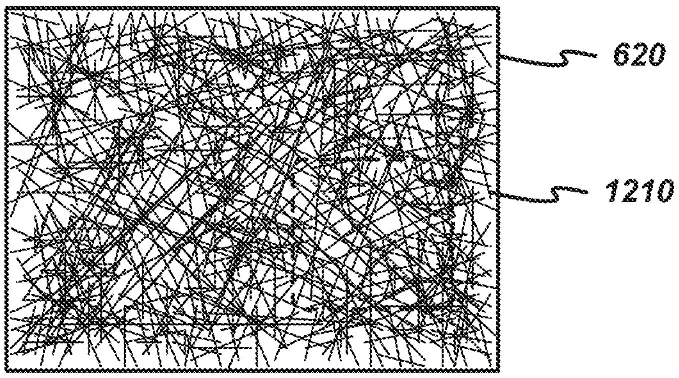
FIG. 12 illustrates a front view of another alternative detection element of an integrated explosive detector of one or more embodiments described herein.

FIG. 12 illustrates a front view of another alternative detection element 620 of an integrated explosive detector 100. In this example, the detection element 620 may include a matrix of painted or otherwise deposited nanowires.

Each detection element 620 may include various detection components, such as photoluminescent polymer fibers 1210. Such detection components may be embedded in, attached to, and/or otherwise integrated into the detection element 620.

Some embodiments may include multiple detection element 620 types or components. For instance, in some embodiments, the detection element 620 may include a felt layer at least partly covered by a nanowire grid or deposited nanowires.

Different embodiments of the detection element 620 may include various other components or features. For instance, some embodiments may include a woven fabric or cloth that includes detection fibers, threads, or other components. As another example, detection fibers may be embedded into pressed paper or cardboard that may include slots or holes.

Figure 13:
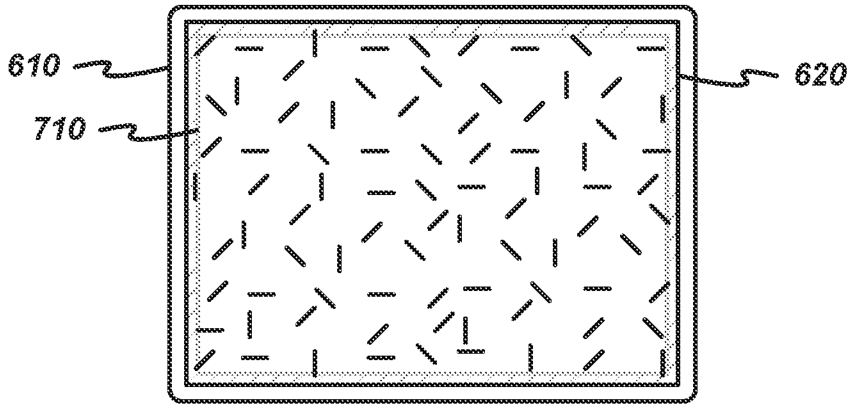
FIG. 13 illustrates a front view of a substrate element and detection element of an integrated explosive detector of one or more embodiments described herein.

FIG. 13 illustrates a front view of a substrate element 610 and detection element 620 of an integrated explosive detector 100. In this example, a felt detection element 620 is combined with a single port 710 base element 610.

Figure 14:
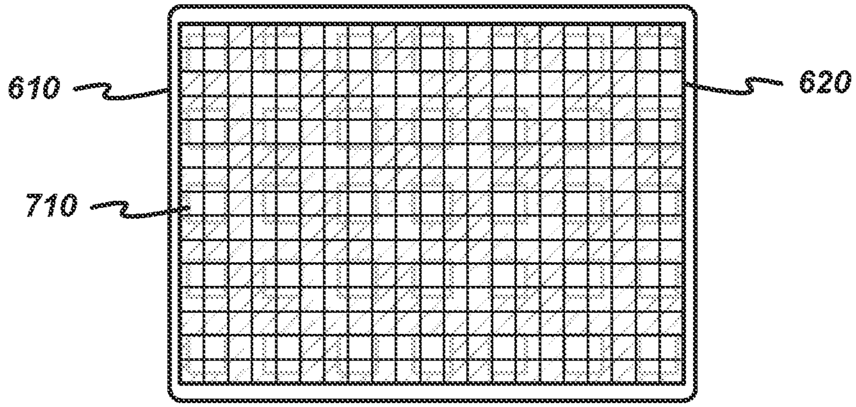
FIG. 14 illustrates a front view of an alternative substrate element and detection element of an integrated explosive detector of one or more embodiments described herein.

FIG. 14 illustrates a front view of an alternative substrate element 610 and detection element 620 of an integrated explosive detector 100. In this example, a multi-port array substrate element 610 is combined with a nanowire grid detection element 620.

Figure 15:
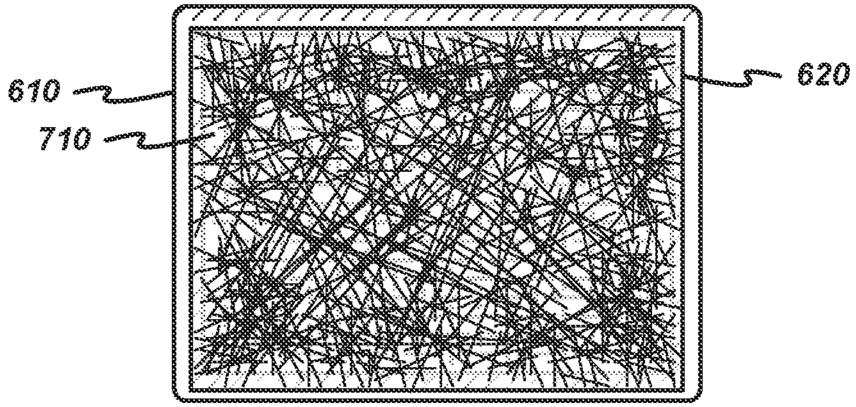
FIG. 15 illustrates a front view of another alternative substrate element and detection element of an integrated explosive detector of one or more embodiments described herein.

FIG. 15 illustrates a front view of another alternative substrate element 610 and detection element 620 of an integrated explosive detector 100. In this example, a substrate element 610 may include a mesh fabric port 710 and detection element 620 includes deposited nanowires.

One of ordinary skill in the art will recognize that different embodiments may include or utilize different combinations of elements than those shown. For instance, the deposited nanowire detection element may be combined with a multi-port or single-port substrate 610.

Although the substrate 610 and detection element 620 are showing as having a similar shape and size, different embodiments may include differently sized and/or shaped elements. For instance, the detection layer 620 may overlap a greater or lesser portion of the surround 720.

Figure 16:
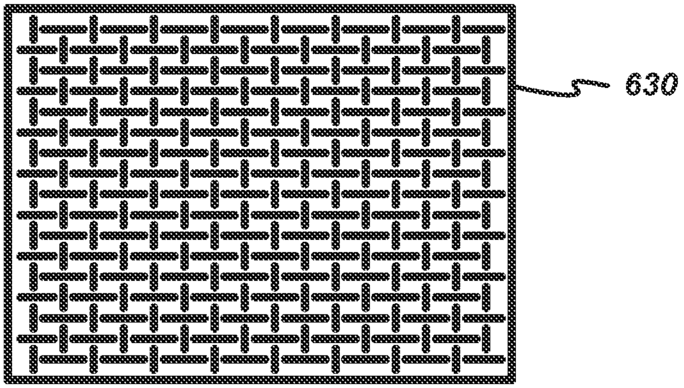
FIG. 16 illustrates a front view of a protective element of an integrated explosive detector of one or more embodiments described herein.

FIG. 16 illustrates a front view of a protective element 630 of an integrated explosive detector 100. In this example, the protective element 630 may include material such as a metal screen or heavy woven fabric that allows fluid such as air to flow under ambient conditions.

Figure 17:
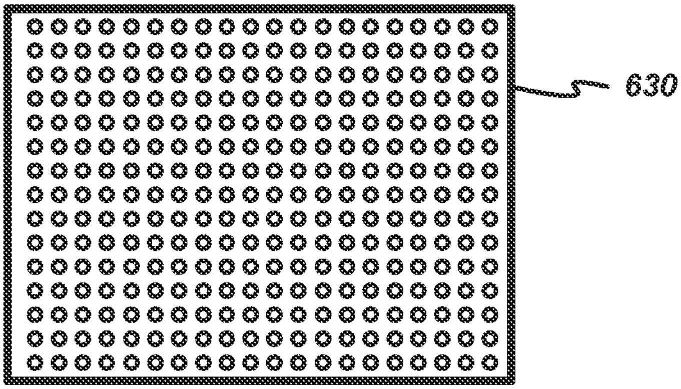
FIG. 17 illustrates a front view of an alternative protective element of an integrated explosive detector of one or more embodiments described herein.

FIG. 17 illustrates a front view of an alternative protective element 630 of an integrated explosive detector 100. In this example, a metal, plastic, or other rigid plate may include multiple through-holes arranged in a matrix or array.

Figure 18:
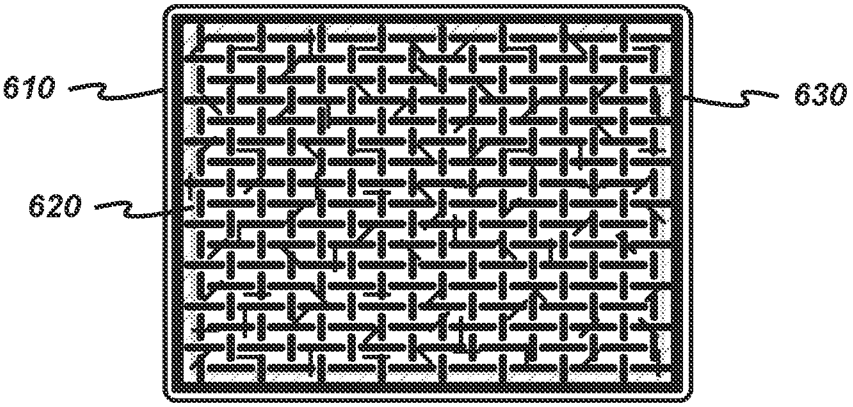
FIG. 18 illustrates a front view of a substrate element, a detection element, and a protective element of an integrated explosive detector of one or more embodiments described herein.

FIG. 18 illustrates a front view of a substrate element 610, a detection element 620, and a protective element 630 of an integrated explosive detector 100. In this example, single-port substrate element 610 is combined with felt detection element 620 and metal screen protective element 630. Different embodiments of the integrated explosive detector 100 may include different combinations of elements, and/or multiple iterations of various element types.

The protective element 630 may be differently sized and/or shaped than shown. For instance, some embodiments may include a round port 710, round surround 720, and round protective element 630.

Figure 19:
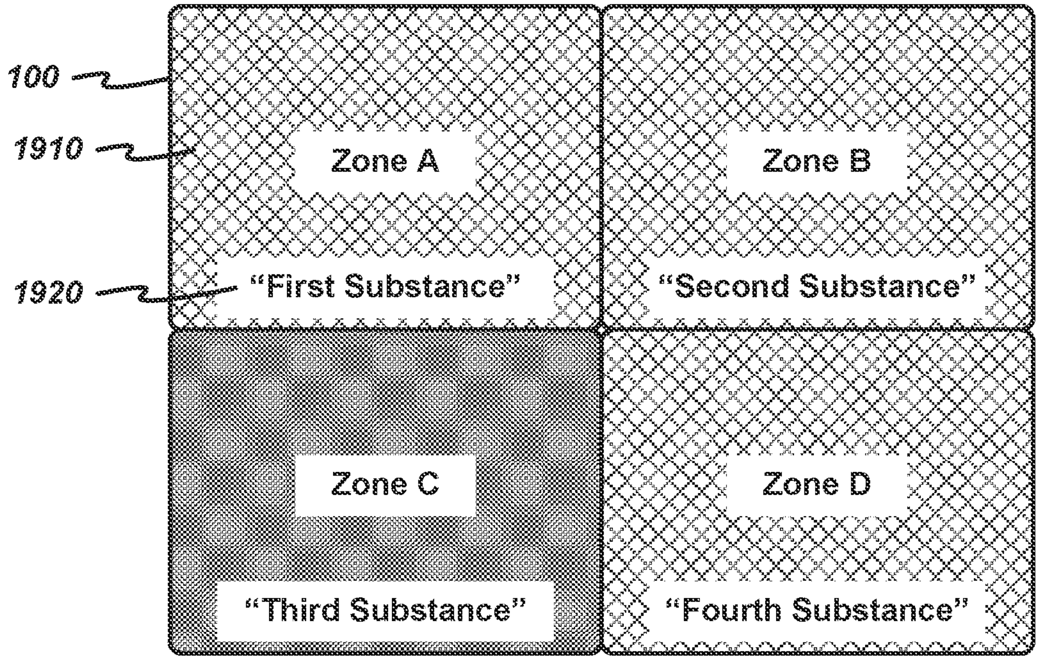
FIG. 19 illustrates a front view of a multi-zone integrated explosive detector of one or more embodiments described herein.

FIG. 19 illustrates a front view of a multi-zone integrated explosive detector 100. In this example, each zone 1910 is associated with a different substance type. Zones 1910 may be associated with other types of indications (e.g., various concentration thresholds). Each indicator or label 1920 may be a visible indicator that is, for example, written or painted onto the zone. Labels 1920 may include, for instance, text, graphics (e.g., icons, images, etc.), textures or other tactile elements, etc. Zones 1910 may be indicated using various delimiting features (e.g., painted or written borders). In some embodiments, zones 1910 may be indicated using different component types such as different types of protective element 630.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items and may be used interchangeably with the phrase "one or more." Where only one item is intended, the terms "one," "single," "only," or similar language is used. Further, the phrase "based on" is intended to mean "based, at least in part, on" unless explicitly stated otherwise.

The foregoing relates to illustrative details of exemplary embodiments and modifications may be made without departing from the scope of the disclosure. Even though particular combinations of features are recited in the claims and/or disclosed in the specification, these combinations are not intended to limit the possible implementations of the disclosure. In fact, many of these features may be combined in ways not specifically recited in the claims and/or disclosed in the specification. For instance, although each dependent claim listed below may directly depend on only one other claim, the disclosure of the possible implementations includes each dependent claim in combination with every other claim in the claim set.

I claim:

1. An integrated explosive detector for a container, the integrated explosive detector comprising:

a substrate element embedded into a surface of the container, the substrate comprising a port and a surround, wherein the port allows ambient air flow through the surface of the container and the substrate element; and a detection element coupled to the substrate element, the detection element comprising:

a visual indicator that provides a visible indication when a subject substance is detected via ambient air flow through at least a portion of the detection element via the port and the substrate element.

2. The integrated explosive detector of claim 1 further comprising a rigid protective element coupled to the detection element.

3. The integrated explosive detector of claim 1, wherein the visual indicator comprises photoluminescent polymer fibers that are activated by nitroaromatic explosive particles.

4. The integrated explosive detector of claim 1, wherein the detection element is one of felt, fabric, screen, nanowire mesh, or nanowire paint.

5. The integrated explosive detector of claim 1, wherein the substrate element comprises peel-and-stick adhesive.

6. The integrated explosive detector of claim 1, wherein the detection element at least partially obstructs airflow through a container port in a surface of the container.

7. The integrated explosive detector of claim 1, wherein the container is a cardboard box or paper envelope.

8. A container comprising:

an integrated explosive detector comprising:

a substrate element embedded into a surface of the container, the substrate comprising a port and a surround, wherein the port allows ambient air flow through the surface of the container and the substrate element; and a detection element coupled to the substrate element, the detection element comprising:

a visual indicator that provides a visible indication when a subject substance is detected via ambient air flow through at least a portion of the detection element via the port and the substrate element.

9. The container of claim 8, the integrated explosive detector further comprising a rigid protective element coupled to the detection element.

10. The container of claim 8, wherein the visual indicator comprises photoluminescent polymer fibers that are activated by nitroaromatic explosive particles.

11. The container of claim 8, wherein the detection element is one of felt, fabric, screen, nanowire mesh, or nanowire paint.

12. The container of claim 8, wherein the substrate element comprises peel-and-stick adhesive.

13. The container of claim 8, wherein the detection element at least partially obstructs airflow through a container port in a surface of the container.

14. The container of claim 8, wherein the container is a cardboard box or paper envelope.

* * * * *